United States Patent
Ishii et al.

[11] Patent Number: 6,124,347
[45] Date of Patent: Sep. 26, 2000

[54] CHROMENE DERIVATIVES AND SALTS THEREOF, AND PHARMACEUTICALS CONTAINING THE SAME

[75] Inventors: Fumio Ishii, Sendai; Haruyoshi Honda; Fujiko Konno, both of Tomisato-machi; Tomomi Okada, Yachiyo; Terumitsu Kaihoh, Narita; Yoshihiro Nagao, Narita; Susumu Sato, Narita; Hideaki Matsuda, Abiko, all of Japan

[73] Assignee: SSP Co., Ltd., Tokyo, Japan

[21] Appl. No.: 09/162,451

[22] Filed: Sep. 29, 1998

[30] Foreign Application Priority Data

Sep. 30, 1997 [JP] Japan ..................... 9-266099

[51] Int. Cl.⁷ .................... A61K 31/353; C07D 311/60
[52] U.S. Cl. .......................... 514/456; 549/407
[58] Field of Search .................. 514/456; 549/407

[56] References Cited

FOREIGN PATENT DOCUMENTS

| 0 363 789 | 4/1990 | European Pat. Off. |
| 0 412 939 | 2/1991 | European Pat. Off. |
| 0 605 728 | 7/1994 | European Pat. Off. |
| WO 90/08763 | 8/1990 | WIPO |

OTHER PUBLICATIONS

Patent Abstract of Japan, vol. 97, No. 6, Jun. 30, 1997, JP 09 040626, Feb. 10, 1997.
Patent Abstract of Japan, vol. 97, No. 7, Jul. 31, 1997, JP 09 059233, Mar. 4, 1997.

*Primary Examiner*—Johann Richter
*Assistant Examiner*—Taofiq A. Solola
*Attorney, Agent, or Firm*—Oblon, Spivak, McClelland, Maier & Neustadt, P.C.

[57] ABSTRACT

Disclosed are chromene derivatives represented by the following formula:

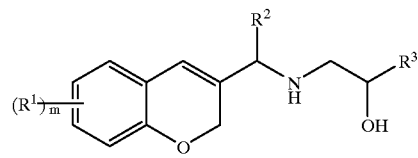

wherein $R^1$s represent alkyl, alkoxy or like groups, $R^2$ represents a hydrogen atom or an alkyl group, $R^3$ represents a substituted or unsubstituted phenyl, naphthyl or heterocyclic group, and m stands for an integer of from 0 to 4, and their salts; and pharmaceuticals containing them as effective ingredients. The chromene derivatives and their salts show excellent AGE formation inhibitory action and are useful as preventives and therapeutics for diabetic complications.

3 Claims, No Drawings

CHROMENE DERIVATIVES AND SALTS THEREOF, AND PHARMACEUTICALS CONTAINING THE SAME

BACKGROUND OF THE INVENTION a) Field of the Invention

This invention relates to novel chromene derivatives and salts thereof, and specifically chromene derivatives and salts thereof, which have inhibitory action against the formation of advanced glycation end-products (AGE) and are useful as pharmaceuticals for the prevention and treatment of various adult diseases, especially diabetic complications, and also to pharmaceuticals containing them as effective ingredients.

b) Description of the Related Art

A diabetic also tends to develop at a high incidence one or more diabetic complications such as cardiovascular diseases, nephropathy, blindness and/or neuropathic aches, although the mechanisms of their developments have not been elucidated. In recent years, however, both abnormality in polyol pathway and sthenia of glycation have been attracting increasing attention as dysbolism induced by high blood glucose levels. Further, it has recently become increasingly evident that the reaction between amino compounds and reducing sugar, said reaction being known in the field of food chemistry, that is, the Maillard reaction proceeds in the living body to glycosylate a surprisingly wide variety of bioproteins and is strongly associated with causes for adult diseases, such as diabetes, and aging. It has been ascertained that this Maillard reaction on the living body results in the gradual formation of advanced glycation end-products (AGE) through complex intramolecular reconstitution. Accumulation of AGE in the body reduces the inherent functions of individual proteins, and is accordingly considered to be one of causes for diseases induced by such reductions, for example, diabetic complications, arteriosclerosis and aging-related diseases such as retinopathy, nephropathy, cardiovascular diseases, neurosis and cataract.

Under continued high blood glucose conditions like diabetes or by aging, many of bioproteins are considered to be subjected to glycation. Among such bioproteins, especially those slow in turnover, for example, collagen, free lens crystallin which does not undergo any turnover, and the like have been proven to undergo the latter-stage Maillard reaction.

As therapeutics for adult diseases, especially diabetic complications, said therapeutics having been developed by paying attention to the Maillard reaction on the living body, the compounds disclosed in JP kokai 9-40626 and JP kokai 9-59233 have been reported but nothing has been put on the market yet. Only aminoguanidine is in the stage of clinical tests.

SUMMARY OF THE INVENTION

An object of the present invention is therefore to provide a compound, which strongly inhibits the formation of AGE and is useful as a preventive and therapeutic for various adult diseases, especially diabetic complications.

With the foregoing circumstances in view, the present inventors synthesized a variety of compounds and proceeded with extensive research on their AGE formation inhibitory action. As a result, it has been found that novel chromene derivatives represented by the below-described formula (1) have excellent inhibitory activities against the formation of AGE and are useful as agents for the prevention and treatment of adult diseases, especially diabetic complications, leading to the completion of the present invention.

The present invention therefore provides a chromene derivative represented by the following formula (1):

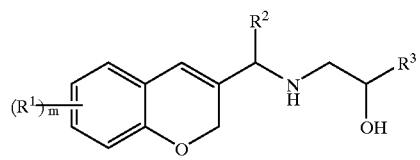

wherein m $R^1$s may be the same or different and each independently represent a halogen atom or an alkyl, alkoxy, halogenoalkyl, hydroxy, amino, aminoalkyl, nitro, cyano, carbamoyl, acyl, alkoxycarbonyl, carboxy, alkoxycarbonylalkyloxy, hydroxyalkyloxy, benzyloxy, sulfonamido, or substituted or unsubstituted phenyl group, $R^2$ represents a hydrogen atom or an alkyl group, $R^3$ represents a substituted or unsubstituted phenyl, naphthyl or heterocyclic group, and m stands for an integer of from 0 to 4, or a salt thereof; and a pharmaceutical comprising the chromene derivative or the salt thereof as an effective ingredient.

As the chromene derivative or the salt thereof according to the present invention shows excellent inhibitory action against the formation of advanced glycation end-products (AGE), it is useful as a pharmaceutical for the prevention and treatment of various adult diseases, especially diabetic complications.

DETAILED DESCRIPTION OF THE INVENTION AND PREFERRED EMBODIMENTS

In the chromene derivative (1) according to the present invention, the alkyl groups represented by $R^1$ and $R^2$ in the formula (1) may preferably be those having 1 to 6 carbon atoms, for example, linear or branched $C_{1-6}$ alkyl groups such as methyl, ethyl, n-propyl, i-propyl, n-butyl, i-butyl, sec-butyl, t-butyl, n-pentyl, i-pentyl, n-hexyl or i-hexyl groups. As the alkoxy group represented by $R^1$, linear or branched alkoxy groups having 1 to 6 carbon atoms are preferred, including, for example, methoxy, ethoxy, n-propoxy, i-propoxy, n-butoxy, i-butoxy, sec-butoxy, t-butoxy, n-pentyloxy, i-pentyloxy, n-hexyloxy and i-hexyloxy. Illustrative of the halogen atom are fluorine, chlorine, bromine and iodine atoms. Examples of the halogenoalkyl group can include linear or branched alkyl groups having 1–6 carbon atoms and substituted by one or more of such halogen atoms. As the acyl group, $C_{1-6}$ alkanoyl groups and $C_{7-11}$ aroyl groups are preferred, and specific examples can include formyl, acetyl, propionyl, n-butyryl, i-butyryl, n-valeryl, i-valeryl, pivalyl, benzoyl and naphthoyl. Examples of the alkyl and alkoxy moieties in the aminoalkyl, alkoxycarbonyl, alkoxycarbonylalkyloxy and hydroxyalkyloxy groups can include those mentioned above, with methyl, ethyl, methoxy and ethoxy being preferred. Further, examples of one or more substituent groups for the phenyl group can include halogen atoms and alkyl, alkoxy, halogenoalkyl, hydroxy, amino, aminoalkyl, nitro, cyano, carbamoyl, acyl, alkoxycarbonyl, carboxy, alkoxycarbonylalkyloxy, hydroxyalkyloxy, benzyloxy, and sulfonamido groups. As $R^1$, a methoxy, hydroxy, methoxycarbonylmethoxy or 2-hydroxyethoxy group or the like is preferred. In addition, as $R^2$, a hydrogen atom or a methyl group is preferred.

Examples of the heterocyclic group represented by $R^3$ can include heteromonocyclic groups such as pyridyl, pyrimidyl and pyridazinyl and heterobicyclic groups such as quinolyl, isoquinolyl, quinazolyl and quinoxalyl.

Examples of substituent groups for the phenyl, naphthyl and heterocyclic groups represented by $R^3$ can include halogen atoms; alkyl, alkoxy, halogenoalkyl, hydroxy, amino, aminoalkyl, nitro, cyano, carbamoyl, acyl, alkoxycarbonyl, carboxy, alkoxycarbonylalkyloxy, hydroxyalkyloxy, benzyloxy and sulfonamido groups; and substituted or unsubstituted phenyl groups. Preferred examples can include chlorine atom and methoxy, hydroxy, benzyloxy and methoxycarbonyl groups. The phenyl, naphthyl and heterocyclic groups may each contain these substituent groups preferably as many as 0 to 5, with 0 to 3 being particularly preferred. Although m stands for an integer of 0 to 4, 0 or 1 is preferred.

No particular limitation is imposed on the salt of the chromene derivative (1) according to the present invention insofar as it is a pharmaceutically acceptable salt. Preferred examples of such salts can include hydrogen halides such as hydrofluoride, hydrochloride, hydrobromide and hydroiodide; inorganic salts such as carbonate, nitrate, perchlorate, sulfate and phosphate; lower alkylsulfonates such as methanesulfonate, ethanesulfonate, trifluoromethanesulfonate; arylsulfonates such as benzenesulfonate and p-toluenesulfonate; organic acid salts such as fumarate, maleate, succinate, citrate, tartrate and oxalate; amino acid salts such as glutamate and aspartate; and salts with alkali metals and alkaline earth metals such as sodium, potassium and calcium.

In addition, the present invention also include hydrates, pharmaceutically-acceptable various solvates, polymorphous forms and the like of the chromene derivative of the above formula (1). Moreover, the present invention also include stereoisomers of the chromene derivative with respect to the asymmetric carbon in the formula (1).

The chromene derivative (1) according to the present invention can be synthesized, for example, in accordance with the following scheme. Synthesis process wherein $R^1$, $R^2$, $R^3$ and m have the same meanings as defined above.

Namely, the compound (2) and nitromethane are reacted in the presence of a suitable base into the compound (3) (step 1), which is then reduced into the compound (4) (step 2). As an alternative, the compound (4) can also be synthesized by reducing the cyanohydrin which is prepared by reacting the compound (2) with trimethylsilyl cyanide (step 3). Finally, the compound (4) and the compound (5) are condensed and the resulting condensation product is then reduced, whereby the compound (1) according to the present invention can be synthesized (step 4). A description will hereinafter be made about each of the steps.

Step 1

Using nitromethane in an amount equivalent to or greater than the compound (2), the reaction is conducted in the presence of the base.

Suitable examples of the base for use in the reaction can include sodium methoxide, sodium ethoxide, potassium t-butoxide, sodium hydride, and calcium hydride. No particular limitation is imposed on the solvent for use in the reaction insofar as the solvent does not affect the reaction. Examples of the solvent can include alcohols such as methanol and ethanol; ethers such as diethyl ether and tetrahydrofuran; dimethylformamide; and dimethyl sulfoxide.

Step 2

Catalytic hydrogenation of the compound (3) in the presence of an adequate catalyst and solvent makes it possible to synthesize the compound (4). It is preferred to conduct the reaction in the presence of a solvent such as methanol, ethanol or dioxane for 1 to 24 hours while using, as a catalyst, palladium on charcoal, palladium black, platinum oxide, Raney nickel or the like.

Step 3

The compound (4) can be synthesized by reacting the compound (2) and trimethylsilyl nitrile into the corresponding cyanohydrin in the presence of a catalyst such a zinc iodide in a solvent such as dichloromethane, chloroform or

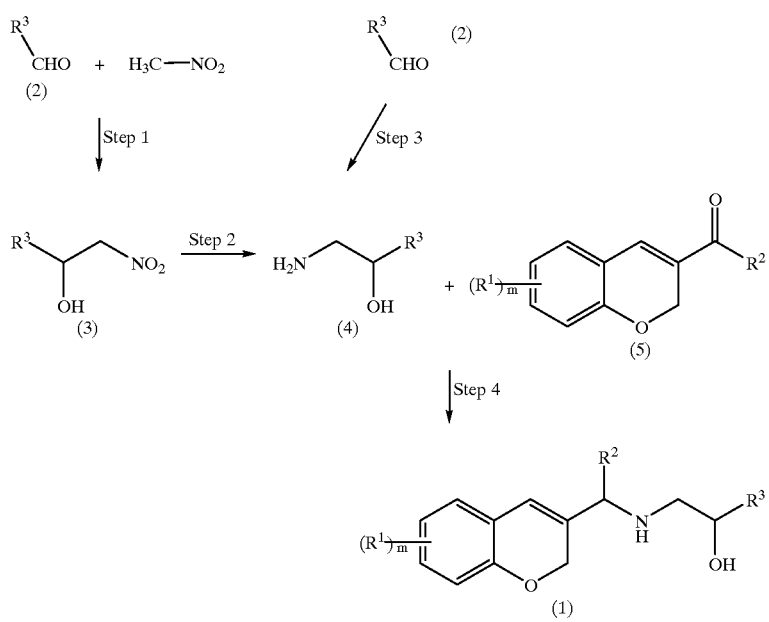

nitromethane, distilling off the solvent under reduced pressure, adding a solvent such as diethyl ether or tetrahydrofuran to the residue and then conducting a reducing reaction with a reducing agent such as lithium aluminum hydride or lithium borohydride.

Step 4

The chromene derivative of the formula (1) can be synthesized by reacting the chromene derivative (5) and the 2-amino-1-substituted ethanol derivative (4) in the presence of an acid catalyst and reducing the thus-obtained imine derivative with an appropriate reducing agent. The chromene derivative (5) can be easily synthesized by a known process [for example, Journal of Organic Chemistry, 39, 2426 (1974)]. As the acid catalyst for use in the reaction, acetic acid, p-toluenesulfonic acid, methanesulfonic acid, titanium tetrachloride or the like can be used. No particular limitation is imposed on the solvent insofar as the reaction is not affected. Usable examples of the solvent can include alcohols such as methanol, ethanol, n-propanol and ethoxyethanol; chlorinated hydrocarbons such as dichloromethane and chloroform; and hydrocarbons such as benzene and toluene. Examples of the appropriate reducing agent for use in the reaction can include sodium borohydride and sodium cyanoborohydride. The reaction may be conducted under ice cooling or with heating under reflux, and the reaction time may range from 1 to 24 hours or so.

Isolation and purification of the target compounds in the above reactions can be conducted in a manner known per se in the art, for example, by washing, extraction, recrystallization, chromatography and/or the like.

The compound (1) according to the present invention shows excellent AGE formation inhibitory action, so that it is useful as an agent for the prevention and treatment of adult diseases, especially diabetic complications.

To use the compound (1) according to the present invention as such a pharmaceutical, it is only necessary to mix it with a solid or liquid carrier known in the present field of art and then to formulate it into a medicinal composition (medicinal preparation) suitable for parenteral administration, oral administration or external administration.

Examples of the medicinal preparation can include liquid preparations such as injections, inhalants, syrups and emulsions; solid preparations such as tablets, capsules and granules; and external preparations such as ointments and suppositories. These preparations may contain additives commonly employed in the art—such as dissolution aids, stabilizers, humectants, emulsifiers, absorption enhancers and surfactants—as needed. Illustrative of usable excipients are injection-grade distilled water, Ringer's injection, glucose, sucrose syrup, gelatin, edible oil, cacao butter, magnesium stearate and talc.

When the compound (1) according to the present invention is used as an agent for the prevention and treatment of adult diseases, especially diabetic complications, its dose to an adult patient may preferably range from 1 to 1,000 mg per day in the case of oral administration although the dose varies depending on the administration method and the age and weight of the patient. Incidentally, use of the compound (1) of the present invention is not limited to human being, but the compound (1) can also be used for other mammals as a veterinary drug.

The present invention will next be described more specifically by the following Synthesis Examples, Examples and Test. It should however be borne in mind that they are merely illustrative and they by no means limit the present invention.

Synthesis Example 1

Synthesis of 1-[3,5-dimethoxy-4-(methoxymethoxy) phenyl]-2-nitro-1-ethanol (Compound (3))

To a dissolved solution of sodium (2.54 g, 0.111 mol) in anhydrous methanol (70 ml) was added nitromethane (7.07 g, 0.116 mol) at room temperature. A solution of 3,5-dimethoxy-4-(methoxymethoxy)benzaldehyde (23.8 g, 0.1053 mol) in methanol (70 ml) was added dropwise, and the resulting mixture was stirred for 3 hours. After completion of a reaction, diethyl ether (500 ml) was added and precipitated crystals were collected by filtration. The crystals were suspended in diethyl ether (500 ml). At 0°C., acetic acid (6.4 g, 0.107 mol) was added, followed by stirring for 12 hours. After insoluble matter was filtered off, the filtrate was concentrated. The resulting crystals were washed with hexane, whereby the title compound (15.42 g) was obtained as pale yellow crystals. The filtered-off insoluble matter was dissolved in water, followed by extraction with ethyl acetate. The extract was dried over anhydrous sodium sulfate and the solvent was removed, whereby the title compound (1.0 g) was obtained additionally.

Total yield: 16.42 g (54.6%).

NMR (CDCl$_3$, δ): 3.06(1H,d), 3.59(3H,s), 3.85(6H,s), 4.46–4.61(2H,m), 5.10(2H,s), 5.40(1H,br), 6.60(2H,s).

Synthesis Example 2

Synthesis of 2-amino-1-[3,5-dimethoxy-4-(methoxymethoxy)phenyl]-1-ethanol (Compound (4))

To a solution of 1-[3,5-dimethoxy-4-(methoxymethoxy)-phenyl]-2-nitro-1-ethanol (11.78 g, 41.0 mmol) in ethanol (100 ml) was added 10% palladium on charcoal (3.5 g), followed by hydrogenation at room temperature for 6 hours. After completion of the reaction, the catalyst was filtered off. The filtrate was concentrated, whereby the title compound (8.57 g, yield: 81.6%) was obtained as colorless crystals.

NMR (CDCl$_3$, δ): 2.60–3.10(2H,m), 3.60(3H,s), 3.85(6H, s), 4.50–4.63(1H,m), 5.10(2H,s), 6.59(2H,s).

Synthesis Example 3

Synthesis of 2-amino-1-(3,4-dimethoxyphenyl)-1-ethanol (Compound (4))

To a stirred solution of veratraldehyde(16.6 g) and zinc iodide (50 mg) in anhydrous nitromethane (200 ml) was added trimethylsilyl cyanide (12 g) dropwise under nitrogen. After the resulting mixture was stirred at room temperature for 1 hour, the solvent was removed under reduced pressure. Anhydrous tetrahydrofuran (50 ml) was added to the residue, and the resulting mixture was added under ice cooling to a suspension of lithium aluminum hydride (3.9 g) in anhydrous tetrahydrofuran (200 ml). After that, the resulting mixture was stirred for 1 hour at room temperature. Water was added to the reaction mixture, insoluble matter was filtered off, and the solvent was then removed under pressure from the filtrate. Chloroform (300 ml) was added to the residue. The resulting mixture was washed with water and was then dried over anhydrous sodium sulfate. The solvent was removed under reduced pressure. The thus-obtained residue was purified by a silica gel column, whereby the title compound (10.8 g, yield: 54.8%) was obtained as colorless crystals.

NMR (CDCl$_3$, δ): 2.3(3H,s), 2.75–2.95(2H,m), 3.85(6H, s), 4.4–4.7(1H,m), 6.8–7.0(3H,m).

EXAMPLE 1

Synthesis of 4-{2-[(2H-3-chromenylmethyl)amino]-1-hydroxyethyl}-2,6-dimethoxyphenol (Invention Compound 9)

2-Amino-1-[3,5-dimethoxy-4-(methoxymethoxy)phenyl]-1-ethanol (Compound (4)) (5.0 g, 19.5 mmol) and 2H-3-chromenaldehyde (3.12 g, 19.5 mmol) were dissolved in chloroform (80 ml). After adding a single droplet of titanium tetrachloride to the resulting solution, it was heated under reflux for 1 hour. After the reaction mixture was allowed to cool down, insoluble matter was filtered off and the filtrate was then concentrated. The residue so obtained was dissolved in methanol (40 ml), to which sodium borohydride (2.5 g, 66.0 mmol) was added in small portions under ice cooling. The resulting mixture was stirred for 2 hours, during which the temperature of the mixture went up from the temperature of ice cooling to room temperature. After completion of the reaction, the solvent was removed and water was added to the residue. The resulting mixture was neutralized with acetic acid and was then extracted with ethyl acetate. After the extract was dried over anhydrous magnesium sulfate, the solvent was removed. The residue was dissolved in ethanol (30 ml), to which a saturated hydrochloric acid-ethanol solution (1 ml) was added. The resulting solution was stirred for 1 hour. Water was added to the reaction mixture. The resulting mixture was basified with aqueous ammonia, followed by extraction with chloroform. After the extract was dried over anhydrous magnesium sulfate, the solvent was removed. The residue was purified by column chromatography on a silica gel and was then recrystallized from ethanol, whereby Invention Compound 9 (3.30 g, yield: 47.4%) was obtained as colorless crystals.

EXAMPLES 2–22

Following the procedures of Example 1, Compounds 1 to 8 and 10 to 22 which will be shown next in Table 1 to Table 5 were synthesized.

TABLE 1

| Comp'd No. | R¹ | R² | R³ | NMR (CDCl₃, δ) |
|---|---|---|---|---|
| 1 | H | H | (4-OMe, 3-OMe phenyl) | 2.45(2H, br s), 2.7–2.9 (2H, m), 3.3(2H, s), 3.85(6H, s), 4.5–4.8 (3H, m), 6.25(1H, br s), 6.6–7.1(7H, m) |
| 2 | H | H | (4-OBn phenyl) | 2.2–2.8(4H, m), 3.25(2H, s), 4.5–4.8 (3H, m), 4.95(2H, s), 6.2(1H, s), 6.6–7.5 (13H, m) |
| 3 | H | H | (2-Cl phenyl) | 2.15–3.2(4H, m), 3.3(2H, s), 4.85(2H, s), 5.1(1H, dd), 6.3 (1H, s), 6.5–7.7 (8H, m) |
| 4 | H | H | (phenyl) | 2.0–3.0(4H, m), 3.35 (2H, s), 4.6–4.9 (3H, m), 6.35(1H, s), 6.7–7.2(4H, m), 7.3–7.45(5H, m) |

TABLE 1-continued

| Comp'd No. | R¹ | R² | R³ | NMR (CDCl₃, δ) |
|---|---|---|---|---|
| 5 | H | H | (4-OH phenyl) | 2.8(2H, d), 3.3(2H, s), 4.05(3H, s), 4.6–4.8 (3H, m), 6.35(1H, s), 6.7–7.35(8H, m), (CDCl₃ + CD₃OD) |
| 6 | H | H | (3-OH phenyl) | 2.68(2H, d), 3.16(2H, s), 4.6(4H, br), 4.84 (2H, s), 6.16(1H, s), 6.6–7.28(8H, m) |

TABLE 2

| Comp'd No. | R¹ | R² | R³ | NMR (CDCl₃, δ) |
|---|---|---|---|---|
| 7 | H | H | (3-OH, 4-OMe phenyl) | 2.78(2H, d), 3.33(2H, s), 3.86(6H, s), 4.5–4.83(3H, m), 6.3 (1H, s), 6.6–7.15(7H, m), (CDCl₃ + CD₃OD) |
| 8 | H | H | (3-OMe, 4-OH phenyl) | 2.78(2H, d), 3.3(2H, s), 3.56(3H, s), 3.83(3H, s), 4.53–4.83 (3H, m), 6.28(1H, s), 6.63–7.13(7H, m), (CDCl₃ + CD₃OD) |
| 9 | H | H | (3-OMe, 4-OH, 5-OMe phenyl) | 2.60–3.70(5H, m), 3.38(2H, s), 3.89(6H, s), 4.70(1H, s), 4.78 (2H, s), 6.32–7.17 (7H, m) |
| 10 | H | H | (3-OBn, 4-OBn, 5-OBn phenyl) | 2.5–2.89(3H, m), 3.3 (2H, br). 4.43–4.83 (4H, m), 5.03(2H, s), 5.1(4H, s), 6.3(1H, br s), 6.66(2H, s), 6.79–7.53(19H, m) |
| 11 | H | H | (3-OBn, 5-OBn phenyl) | 2.18(2H, br), 2.66–2.96(2H, m), 3.33(2H, s), 4.5–4.83 (3H, m), 5.03(4H, s), 6.30(1H, br s), 6.43–7.50(17H, m) |

TABLE 3
| Comp'd No. | R¹ | R² | R³ | NMR (CDCl₃, δ) |
|---|---|---|---|---|
| 12 | 8-OMe | H | 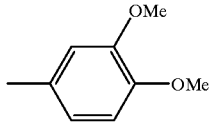 | 2.5–3.0(4H, m), 3.3(2H, br s), 3.8(9H, s), 4.5–4.85(3H, m), 6.3(1H, br s), 6.5–7.0(6H, m) |
| 13 | 8-OMe | H | 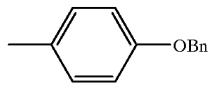 | 2.2–2.9(4H, m), 3.25(2H, s), 3.8 (3H, s), 4.5–4.8(3H, m), 4.95 (2H, s), 6.2(1H, s), 6.4–7.0 (12H, m) |
| 14 | 8-OMe | H | 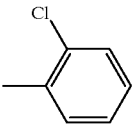 | 2.1–3.2(4H, m), 3.35(2H, s), 3.85(3H, s), 4.85(2H, s), 5.15 (1H, dd), 6.3(1H, s), 6.5–6.9 (3H, m), 7.1–7.7(4H, m) |
| 15 | 8-OMe | H | 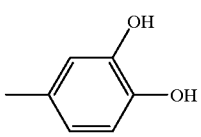 | 2.56–2.58(2H, m), 3.26(2H, s), 3.73(3H, s), 4.44–4.48(1H, m), 4.66(2H, s), 6.31(1H, s), 6.55–6.66(3H, m), 6.73–6.83 (3H, m), (DMSO-d₆) |
| 16 | 8-OMe | H | 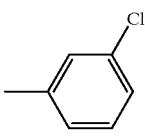 | 2.0–3.0(4H, m), 3.32(2H, s), 3.84(3H, s), 4.40–5.0(3H, m), 6.2(1H, br s), 6.5–7.6(7H, m) |
TABLE 4
| Comp'd No. | R¹ | R² | R³ | NMR (CDCl₃, δ) |
|---|---|---|---|---|
| 17 | 8-OMe | H | 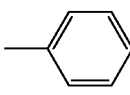 | 2.28(2H, br), 2.52–3.08(2H, m), 3.84(3H, s), 3.92(3H, s), 3.96 (2H, s), 4.60–5.0(3H, m), 6.2–7.0(4H, m), 7.44(2H, d), 8.0(2H, d) |
| 18 | H | Me | 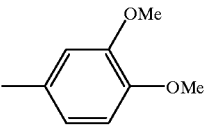 | 2.2(3H, d), 2.3(2H, br s), 2.6–2.85(2H, m), 3.2–3.5(1H, m), 3.8(6H, s), 4.5–4.8(3H, m), 6.2(1H, br s), 6.7–7.1(7H, m) |
| 19 | 7-OH | H | 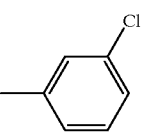 | 2.70–2.80(2H, m), 4.63(2H, s), 4.70–4.73(1H, m), 6.18(1H, s), 6.26–6.30(2H, m), 6.59(2H, s), 6.80(1H, d), 7.28–7.36(4H, m) (DMSO-d₆) (fumarate) |
| 20 | 7-OMe | H | 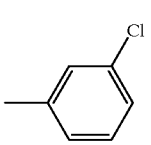 | 2.70–2.89(2H, m), 2.90(2H, s), 3.77(3H, s), 4.73(1H, br), 6.28 (1H, s), 6.38–6.44(2H, m), 6.87(1H, d), 7.22–7.37(4H, m) |

TABLE 4-continued

| Comp'd No. | R¹ | R² | R³ | NMR (CDCl₃, δ) |
|---|---|---|---|---|
| 21 | 7-OCH₂COOMe | H |  | 2.62–2.64(2H, m), 3.23(2H, br), 3.69(3H, s), 4.65–4.70(1H, m), 4.72(2H, s), 5.34(1H, br), 6.27 (1H, s), 6.33–6.43(2H, m), 6.90(1H, d), 7.25–7.39(4H, m) (DMSO-d₆) |

TABLE 5

| Comp'd No. | R¹ | R² | R³ | NMR (CDCl₃, δ) |
|---|---|---|---|---|
| 22 | 7-O(CH₂)₂OH | H |  | 2.62–2.64(2H, m), 3.23(2H, s), 3.65–3.69(2H, m), 3.91–3.94(2H, m), 4.64–4.76(2H, m), 6.26(1H, s), 6.33–6.44(2H, m), 6.89(1H, d), 7.26–7.39(4H, m) (DMSO-d₆) |

Test

With respect to each test compound, solutions of the test compound in dimethyl sulfoxide, said solutions containing said test compound at various concentrations, were each added together with 1 mg/ml of ovolysozyme and 100 mM of xylose to a phosphate-buffered physiological saline of pH 7.4. Each reaction mixture was then incubated at 37° C. for 21 days. A portion of the reaction mixture, said portion being in a predetermined amount, was then separated by sodium lauryl sulfate-polyacrylamide gel electrophoresis (SDS-PAGE). After the electrophoresis, the gel was treated by silver staining to stain proteins. AGE formation inhibitory action of the test compound was calculated in terms of 50% inhibitory concentration by image-processing and analyzing the degree of formation of the dimer (28.8 Kda) of lysozyme (14.4 Kda) relative to that in a control, that is, a reaction mixture not added with the test compound while making use of NIH Image Ver. 1.55. The results are shown in Table 6.

TABLE 6

| Compound No. | IC₅₀ (μg/ml) |
|---|---|
| 6 | 10 |
| 9 | 30 |
| 15 | 3 |
| Amionoguanidine | 30 |

From the above results, the compounds according to the present invention have been found to show inhibitory action against the formation of proteinaceous crosslinks associated with a progress of the Maillard reaction. This action is superior to that of aminoguanidine which is a known Maillard reaction inhibitor. The compounds according to the present invention have therefore been found to have extremely high utility as pharmaceuticals for the prevention and treatment of diabetic complications, arteriosclerosis and aging.

We claim:

1. A chromene derivative represented by the following formula (1):

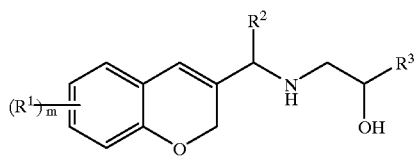

(1)

wherein m R¹s may be the same or different and each independently represent a halogen atom or an alkyl, alkoxy, halogenoalkyl, hydroxy, amino, aminoalkyl, nitro, cyano, carbamoyl, acyl, alkoxycarbonyl, carboxy, alkoxycarbonylalkyloxy, hydroxyalkyloxy, benzyloxy, sulfonamido, or substituted or unsubstituted phenyl group, R² represents a hydrogen atom or an alkyl group, R³ represents a substituted or unsubstituted phenyl, naphthyl or heterocyclic group, and m stands for an integer of from 0 to 4; or a salt thereof.

2. A pharmaceutical composition comprising, as an effective ingredient, a chromene derivative or a salt thereof as defined in claim 1 and a pharmaceutically acceptable carrier.

3. A pharmaceutical composition according to claim 2, which is an agent for the prevention and treatment of diabetic complications.

* * * * *